United States Patent [19]

Gruetzmacher et al.

[11] Patent Number: 4,670,564

[45] Date of Patent: Jun. 2, 1987

[54] PREPARATION OF THIENO-IMIDAZOLE DERIVATIVES

[75] Inventors: Gordon D. Gruetzmacher, Gales Ferry; Robert A. Volkmann, Ledyard, both of Conn.

[73] Assignee: Pfizer Inc., New York, N.Y.

[21] Appl. No.: 711,682

[22] Filed: Mar. 14, 1985

[51] Int. Cl.$^4$ ............................................. C07D 495/04
[52] U.S. Cl. .................................. 548/303; 548/147; 548/154
[58] Field of Search ...................... 548/303, 147, 154

[56] References Cited

U.S. PATENT DOCUMENTS

| | | | |
|---|---|---|---|
| 2,489,235 | 11/1949 | Goldberg et al. | 548/303 |
| 2,489,236 | 11/1949 | Goldberg et al. | 548/303 |
| 3,393,129 | 7/1968 | Shibota et al. | 548/303 |
| 4,029,647 | 6/1977 | Confalone et al. | 548/303 |
| 4,124,595 | 11/1978 | Confalone et al. | 548/303 |
| 4,486,516 | 8/1984 | Volkmann | 548/154 |

OTHER PUBLICATIONS

*Chemical Abstracts,* 98: 199537g (1983) [Penaloza, M., et al., *Rev. Soc. Quim. Mex.* 1982, 26(5), 245–7].
*Chemical Abstracts,* 92: 180975c (1980) [UK 1,551,078, 8/22/79].
Culvenor, C., et al., *J. Chem. Soc.,* 1946, p. 1050.

*Primary Examiner*—Richard A. Schwartz
*Attorney, Agent, or Firm*—Charles J. Knuth; Peter C. Richardson; Mark Dryer

[57] ABSTRACT

A process for the preparation of a thieno-imidazole derivative, particularly descarboxybiotin, a useful intermediate for the preparation of d-biotin, which comprises reacting a thio-substituted intermediate, for example descarboxythiobiotin, with an epoxy compound in an alkanol solvent; and a process for the preparation of said intermediate by reacting a substituted imidazothiazole alcohol with anhydrous hydrogen fluoride.

8 Claims, No Drawings

PREPARATION OF THIENO-IMIDAZOLE DERIVATIVES

BACKGROUND OF THE INVENTION

This invention relates to a process for the preparation of certain thieno-imidazole derivatives including descarboxybiotin. More particularly the invention is concerned with a process for the preparation of descarboxybiotin and a process for the preparation of descarboxythiobiotin. Both descarboxybiotin and descarboxythiobiotin are useful intermediates for the preparation of biotin.

Biotin is a water-soluble vitamin required by higher animals and by many microorganisms. Biosynthesis of biotin by selected yeasts, molds and bacteria is well known. U.S. Pat. No. 3,393,129 discloses the use of a d-biotin-producing strain of bacterium of the genus Sporobolomyces for commercial production of this vitamin. Chemical synthesis is reported in U.S. Pat. Nos. 2,489,235; 2,489,236; 4,029,647 and 4,124,595.

As industrial demand for d-biotin increases, the search for improved synthetic processes continues.

U.S. Pat. No. 4,468,516 discloses a process for the preparation of biotin and certain intermediates useful in such process. Among said intermediates is descarboxybiotin, i.e. the compound hexahydro-2-oxo-4-pentyl-1-H-thieno(3,4-d)-imidazole, of the formula:

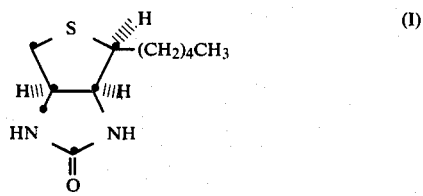

and descarboxythiobiotin, i.e. the compound hexahydro-2-thioxo-4-pentyl-1-H-thieno(3,4-d)imidazole, of the formula:

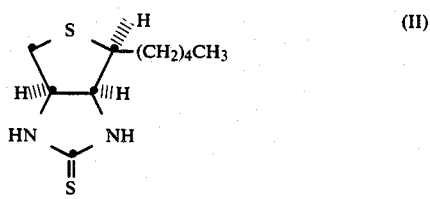

According to the disclosure in U.S. Pat. No. 4,468,516 descarboxybiotin may be prepared by reacting descarboxythiobiotin with a haloalcohol, preferably bromoethanol, in an polar solvent such as ethanol, methoxyethanol or diglyme, and refluxing under an inert gas, preferably nitrogen, until reaction is essentially complete, from 2 to 24 hours, and then treating with a weak base, for example, an alkali metal carbonate, preferably a saturated solution of sodium carbonate.

U.S. Pat. No. 4,468,516 also discloses that the descarboxythiobiotin itself may be prepared by reacting an intermediate alcohol, i.e. tetrahydro-3,3-pentamethylene-7-hydroxymethyl-5-thioxo-1-pentyl-3H,5H-imidazo(1,5c)thiazole, of the formula:

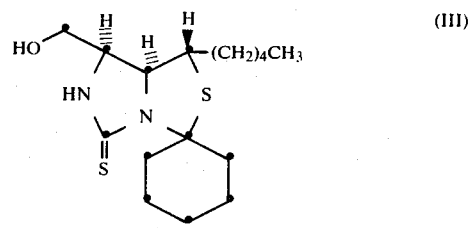

with trifluoroacetic acid.

It has now been found that descarboxybiotin and descarboxythiobiotin may be prepared by improved processes which are superior to the prior art processes for the reasons set out hereinafter. Additionally the processes are applicable to the preparation of other thieno-imidazole derivatives.

SUMMARY OF THE INVENTION

In accordance with the present invention there is provided a process for the preparation of a thienoimidazole derivative having the formula:

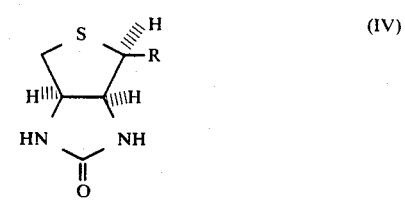

wherein R is $-(CH_2)_4CH_3$, $-(CH_2)_3OR^1$ or $-(CH_2)_5OR^1$, $R^1$ is $(C_1-C_6)$alkyl, $-(CH_2)_4CH$ or $-(CH_2)_4COOR^2$ and $R^2$ is $(C_1-C_6)$alkyl or phenyl; which comprises reacting a compound of the formula:

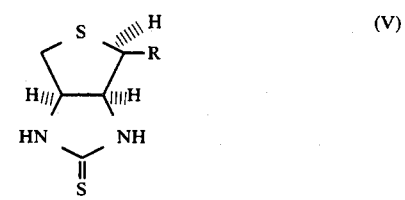

wherein R is as defined above, with an epoxy compound of the formula:

wherein $R^3$ is hydrogen, methyl or $-CH_2OH$; in the presence of an alkanol.

A particularly preferred embodiment of the invention is a process as described above in which the product is descarboxybiotin of formula (I) herein which is prepared by reacting descarboxythiobiotin of formula (II) herein with an epoxy compound of formula (VI) in the presence of an alkanol.

The process according to the invention for preparing descarboxybiotin is superior to prior art processes in that it is cheaper, because of reduced reagent costs; and also it is more productive, because of shorter reaction times and greater concentrations.

The intermediate compound of formula (V) used in the above described process of the invention preferably is prepared by reacting an alcohol of the formula:

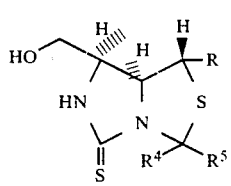
(VII)

wherein R is as defined above R⁴ and R⁵ when taken together form a cycloalkyl group containing 5 or 6 carbon atoms or —CH₂—CH₂—Y—CH₂—CH₂— wherein Y is sulfur, oxygen or NCOOR⁶ wherein R⁶ is ($C_1$-$C_6$)alkyl, or each of R⁴ and R⁵ is ($C_1$-$C_6$)alkyl, ($C_5$-$C_6$)cycloalkyl or phenyl, provided that R⁴ and R⁵ are not both phenyl; with anhydrous hydrogen fluoride in the presence of about two molar equivalents of water per mole of alcohol of formula (VII).

In the formulae set out herein, alkyl is intended to mean an alkyl group containing 1 to 6 carbon atoms and cycloalkyl means a cycloalkyl group containing 5 or 6 carbon atoms. Preferred alkyl groups are methyl and ethyl and the preferred cycloalkyl group is cyclohexyl.

The invention also provides a process for the preparation of a thieno-imidazole derivative having the formula:

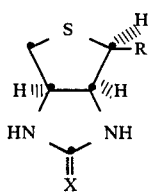
(VA)

wherein R is —(CH₂)₄CH₃, —(CH₂)₃OR¹ or —(CH₂)₅OR¹, wherein R¹ is ($C_1$-$C_6$)alkyl, —(CH₂)₄CN or —(CH₂)₄COOR² and R² is ($C_1$-$C_6$)alkyl or phenyl and X is sulfur or oxygen; which comprises reacting a compound of the formula:

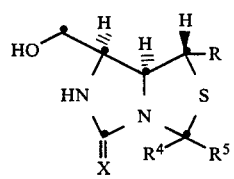
(VIIA)

wherein R and X are as defined above, R⁴ and R⁵ when taken together form a cycloalkyl group containing 5 or 6 carbon atoms or —CH₂—CH₂—Y—CH₂—CH₂— wherein Y is sulfur, oxygen or NCOOR⁶ wherein R⁶ is ($C_1$-$C_6$)alkyl, or each of R⁴ and R⁵ is ($C_1$-$C_6$)alkyl, ($C_5$-$C_6$)cycloalkyl or phenyl, provided that R⁴ and R⁵ are not both phenyl; with anhydrous hydrogen fluoride in the presence of about two molar equivalents of water per mole of the compound of formula (VIIA).

A preferred embodiment of the above process is one in which the product is descarboxythiobiotin of the formula:

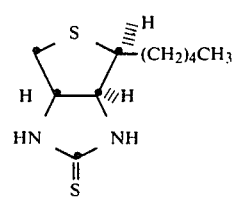
(II)

which is prepared by reacting the alcohol of the formula:

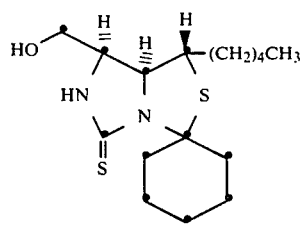
(III)

with anhydrous hydrogen fluoride at a reduced temperature in the presence of about two molar equivalents of water to each mole of alcohol of formula (III).

The process according to the invention for preparing descarboxythiobiotin is superior to prior art processes using other acids in that it provides a higher yield of product, i.e. up to 90%; it is cheaper, because of the low cost of anhydrous hydrogen fluoride; and also it is more productive, because concentrations are increased and work-up is facilitated. A further advantage is that the product prepared by this process is of sufficient purity to be used directly in the further step of preparing descarboxybiotin as described hereinafter.

In carrying out the process of the invention for the preparation of descarboxybiotin the preferred epoxy compound of formula (VI) is ethylene oxide. Other suitable compounds of formula (VI) are propylene oxide and glycidol.

The preferred alkanol is isopropanol.

Preferably, the reaction mixture is heated to a temperature within the range of 50° to 100° C. and maintained at this temperature until the reaction is substantially complete.

In a particularly preferred embodiment descarboxybiotin is prepared from descarboxythiobiotin using ethylene oxide in isopropyl alcohol at a temperature of about 50° C. in a steel autoclave.

DETAILED DESCRIPTION OF THE INVENTION

Descarboxybiotin is a useful intermediate in the synthesis of biotin and descarboxybiotin may be prepared from another useful intermediate descarboxythiobiotin. The steps and reagents leading to the preparation of said intermediates and then to the synthesis of biotin are illustrated in Reaction Scheme A. The formulae set out in the Reaction Scheme and elsewhere herein conform to the accepted convention for indicating stereoisomers, namely " ⫼⫼⫼ " indicates an atom projecting into the plane of the paper (α-orientation), " ◂ " indicates an atom projecting out from the plane of the paper (β-orientation) and "∼∼∼" indicates a substituent which is either in the α or β-orientation.

SCHEME A

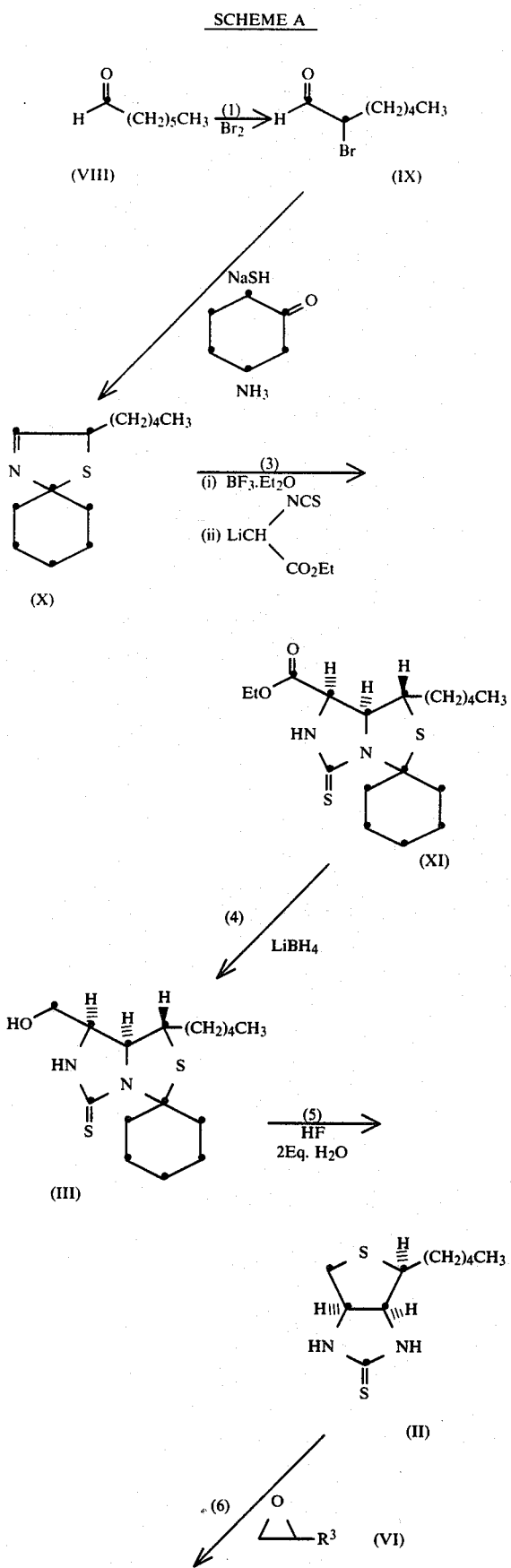

-continued
SCHEME A

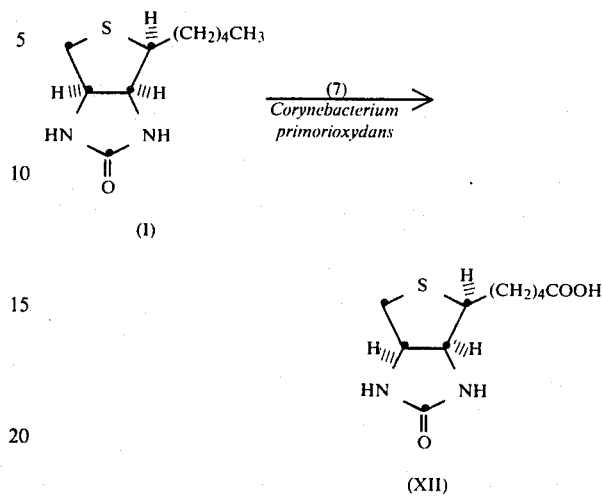

Referring to Reaction Scheme A, in step (1) the heptanal of formula (VIII) is reacted with bromine to form the bromoheptanal of formula (IX); in step (2) the bromoheptanal is reacted with sodium hydrogen sulfide and cyclohexanone followed by the addition of ammonia, according to the method of Thiel, Asinger and Schmiedel (Liebigs Ann. Chem. 611, 121 (1958), to form the thiazoline of formula (X); in step (3) the thiazoline is reacted with boron fluoride ethyl ether and then with lithium ethyl isothiocyanatoacetate to form the cis-ethyl ester of formula (XI); in step (4) the cis-ether of formula (XI) is reduced with lithium borohydride to form the alcohol: tetrahydro-3,3-pentamethylene-7-hydroxymethyl-5-thioxo-1-pentyl-3H,5H-imidazo(1,5c)thiazole (1α, 7β, 7aα), of formula (III); in step (5) the alcohol of formula III is reacted with anhydrous hydrogen fluoride with two molar equivalents of water according to a process of the invention to form descarboxythiobiotin of formula (II); in step (6) the descarboxythiobiotin is reacted with an epoxy compound of formula (VI) wherein $R^3$ is as defined above according to a process of the invention to form descarboxybiotin of formula (I).

The descarboxybiotin is converted to d,-biotin, formula (XII), by microbiological oxidation, for example, with Corynebacterium primorioxydans as illustrated in step (7).

The following Examples illustrate the invention and the manner in which it may be performed.

EXAMPLE 1

Preparation of Descarboxythiobiotin [Step (5) of Reaction Scheme A]

25.0 g (76.1 mmole) of tetrahydro-3,3-pentamethylene-7-hydroxymethyl-5-thioxo-1-pentyl-3H,5H-imidazo(1,5c)thiazole, formula (III), of molecular weight 328.4 and 2.7 g. (150 mmole) of water was introduced into a plastic bottle and the mixture was cooled with an ice bath. 100 ml. of anhydrous hydrogen fluoride was then condensed into the bottle.

Anhydrous hydrogen fluoride (b.p. 19.5° C.) is a toxic, corrosive, colorless gas which must be handled with great care. It was condensed into the plastic bottle from a gas cylinder with ice bath cooling.

After addition of the anhydrous hydrogen fluoride, the resultant brown solution was stirred at room temperature for two hours. The reaction mixture was then poured with cooling into 750 ml. of isopropyl ether in a two liter plastic Erhlenmeyer flask. A white precipitate formed and the mixture was stirred for fifteen minutes.

The white precipitate was collected by vacuum filtration, washed with 100 ml. of cold isopropyl ether and dried under vacuum to give 15.8 g. (68.7 mmole) of descarboxythiobiotin (90% yield; molecular weight 230; mp. 219° to 222° C.). This product is of sufficient purity to be used directly in Step (6).

The combined filtrates containing hydrogen fluoride were neutralized with aqueous potassium hydroxide before disposal.

EXAMPLE 2

Preparation of Descarboxybiotin [Step (6) of Reaction Scheme A]

15.08 g. (68.7 mmole) of descarboxythiobiotin, formula (II), 6.05 g. (137.4 mmole) of ethylene oxide and 175 ml. of isopropanol were introduced into a 300 ml. autoclave. The ethylene oxide (b.p. 10.7° C.) was condensed directly into the autoclave. Alternatively, it may be condensed into a portion of the isopropanol which is then added to the autoclave. Either way, caution must be exercised when handling ethylene oxide, since it is highly toxic.

After introduction of said reagents, the autoclave was sealed and the reaction mixture heated at a temperature of 50° C. for one hour.

The autoclave was cooled and opened, care being exercised to minimize atmospheric contamination. By-products of the reaction are low molecular weight sulfides that have obnoxious odors.

The contents of the autoclave were transferred to a round-bottom flask. The reaction mixture was concentrated to a gummy white solid which was dissolved in 100 ml. of methylene chloride. The organic solution was washed 1× with 100 ml. 0.2N hydrochloric acid, 1× with 100 ml. water and 1× with 100 ml. saturated brine. The organic phase was dried over magnesium sulfate, filtered and concentrated to give a white solid which was collected and dried to give 13.4 g. (62.6 mmole, 91% yield) of descarboxybiotin, mp. 143° to 145° C., molecular weight: 214.

The product had a faint odor of sulfide. However, it was sufficiently pure to be used in Step (7) of Reaction Scheme A.

EXAMPLE 3

Preparation of Descarboxybiotin 230 mg. (1 mmole) of descarboxythiobiotin, 116 mg. (2 mmole) of propylene oxide and 4 ml. of isopropanol were introduced into a small acid digestion bomb and heated at a temperature of 100° C. for 4.5 hours.

The bomb was then cooled to room temperature and opened.

The white slurry was dissolved in chloroform and the resulting solution was extracted with water and saturated brine solution.

The organic solution was dried over magnesium sulfate, filtered and concentrated in vacuo to give 188 mg. (0.879 mmole; 88% yield) of descarboxybiotin, mp. 137° to 140° C.

EXAMPLE 4

Preparation of Descarboxybiotin

Following the same procedure as that used in Example 3, but replacing propylene oxide by glycidol, 230 mg. (1 mmole) of descarboxythiobiotin was reacted with 148 mg. (2 mmole) of glycidol in the presence of 4 ml. of isopropanol.

The said procedure produced 178 mg. (0.832 mmole, 83% yield) of descarboxybiotin, mp. 138° to 142° C.

We claim:

1. A process for the preparation of a thienoimidazole derivative having the formula:

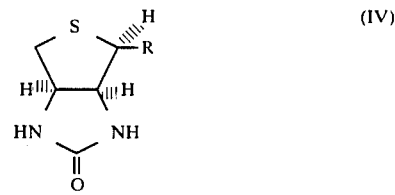

wherein R is $-(CH_2)_4CH_3$, $-(CH_2)_3OR^1$ or $-(CH_2)_5OR^1$, $R^1$ is $(C_1-C_6)$alkyl, $-(CH_2)_4CN$ or $-(CH_2)_4COOR^2$ and $R^2$ is $(C_1-C_6)$alkyl or phenyl; which comprises reacting an alcohol of the formula:

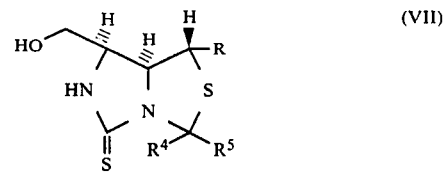

wherein R is as defined above; $R^4$ and $R^5$ when taken together form a cycloalkyl group containing 5 or 6 carbon atoms or $-CH_2-CH_2-Y-CH_2-CH_2-$ wherein Y is sulfur, oxygen or $NCOOR^6$ wherein $R^6$ is $(C_1-C_6)$alkyl, or each of $R^4$ and $R^5$ is $(C_1-C_6)$alkyl, $(C_5-C_6)$cycloalkyl or phenyl, provided that $R^4$ and $R^5$ are not both phenyl; with anhydrous hydrogen fluoride in the presence of about two molar equivalents of water per mole of alcohol of formula (VII) to form a compound of the formula:

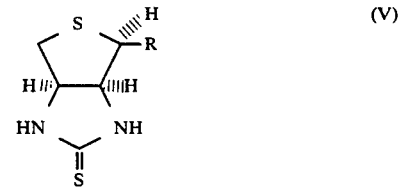

wherein R is as defined above; and reacting the resulting compound of formula (V) with an epoxy compound of the formula:

wherein $R^3$ is hydrogen, methyl or $-CH_2-OH$; in the presence of an alkanol.

2. A process according to claim 11, in which the product is descarboxybiotin of the formula:

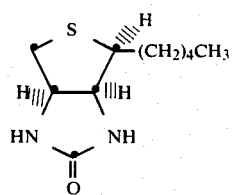
(I)

which is prepared by reacting an alcohol of the formula:

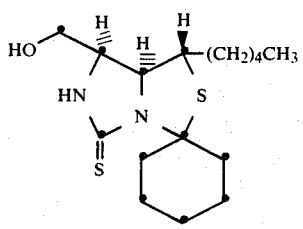
(III)

with anhydrous hydrogen fluoride in the presence of about two molar equivalents of water per mole of alcohol of formula (III) to form descarboxythiobiotin of the formula:

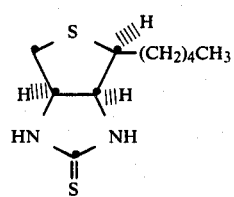
(II)

and reacting said descarboxythiobiotin with said epoxy compound of formula (VI) in the presence of an alkanol.

3. A process according to claim 2, in which the epoxy compound of the formula (VI) is ethylene oxide.

4. A process according to claim 2, in which the epoxy compound of formula (VI) is propylene oxide or glycidol.

5. A process according to claim 2, in which the alkanol is isopropanol.

6. A process according to claim 2, in which the reaction of descarboxythiobiotin with the epoxy compound of formula (VI) is conducted by heating the reaction mixture to a temperature within the range of 50° to 100° C. and maintaining it at this temperature until the reaction is substantially complete.

7. A process for the preparation of a thienoimidazole derivative having the formula:

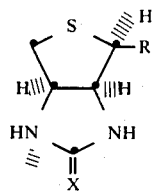
(VA)

wherein R is —(CH$_2$)$_4$CH$_3$, —(CH$_2$)$_3$OR$^1$ or —(CH$_2$)$_5$OR$^1$, wherein R$^1$ is (C$_1$–C$_6$)alkyl, —(CH$_2$)$_4$CN or —(CH$_2$)$_4$COOR$^2$ and R$^2$ is (C$_1$–C$_6$)alkyl or phenyl and X is sulfur or oxygen; which comprises reacting a compound of the formula:

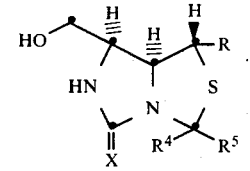
(VIIA)

wherein R and X are as defined above, R$^4$ and R$^5$ when taken together form a cycloalkyl group containing 5 or 6 carbon atoms or —CH$_2$—CH$_2$—Y—CH$_2$—CH$_2$— wherein Y is sulfur, oxygen or NCOOR$^6$ wherein R$^6$ is (C$_1$–C$_6$)alkyl, or each of R$^4$ and R$^5$ is (C$_1$–C$_6$)alkyl, (C$_5$–C$_6$)cycloalkyl or phenyl, provided that R$^4$ and R$^5$ are not both phenyl; with anhydrous hydrogen fluoride in the presence of about two molar equivalents of water per mole of the compound of formula (VIIA).

8. A process according to claim 7 in which the product is descarboxythiobiotin of the formula:

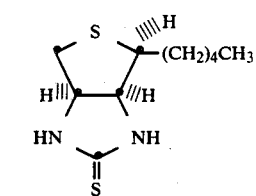
(II)

which is prepared by reacting the alcohol of the formula:

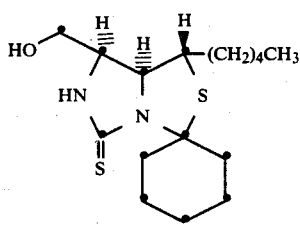
(III)

with anhydrous hydrogen fluoride in the presence of about two molar equivalents of water per mole of alcohol of formula (III).

* * * * *